United States Patent [19]
Sarkadi et al.

[11] Patent Number: 5,872,014
[45] Date of Patent: Feb. 16, 1999

[54] ASSAY FOR MULTI-DRUG RESISTANCE

[76] Inventors: Balazs Sarkadi, 1121 Budapest, Agnes u. 23b; Laszlo Homolya, 1013 Budapest, Krisztina krt. 28; Zsolt Hollo, 1119 Budapest, Allende park 4, all of Hungary

[21] Appl. No.: 928,528

[22] Filed: Sep. 12, 1997

Related U.S. Application Data

[63] Continuation of Ser. No. 322,702, Oct. 13, 1994, abandoned.

[30] Foreign Application Priority Data

Aug. 31, 1994 [HU] Hungary .............................. P9402511

[51] Int. Cl.$^6$ ........................ G01N 33/536; G01N 33/533
[52] U.S. Cl. ......................... 436/536; 436/546; 436/800; 436/808; 435/975
[58] Field of Search .................................. 436/536, 546, 436/800, 808; 435/975

[56] References Cited

U.S. PATENT DOCUMENTS

| | | | |
|---|---|---|---|
| 4,281,061 | 7/1981 | Zuk et al. ..................................... | 435/7 |
| 5,314,805 | 5/1994 | Haugland et al. ......................... | 435/29 |
| 5,407,653 | 4/1995 | Piwnica-Worms ...................... | 424/1.11 |

OTHER PUBLICATIONS

Liminga et al. Experimental Cell Research. 212: 291–296 (Jun. 1994).
Efferth et al. Arzneim–Forsch/Drug Res. 38(11) Nr. 12(1988).
Arceci, R., "Clinical Significance of P–glycoprotein in Multidrug Resistance Malignancies", Journal of American Society of Hematology 81:2215–2222, May 1, 1993.
Bruggemann et al., "Characterization of the Azidopine and Vinblastine Binding Site of P–glycoprotein", The Journal of Biological Chemistry 267:21020–21026, Oct. 15, 1992.
Germann et al., "Expression of the Human Multidrug Transporter in Insect Cells by a Recombinant Baculovirus", Biochemistry 29:2295–2303, 1990.
Gottesman et al., "Biochemistry of Multidrug Resistance Mediated by the Multidrug Transporter", Annu. Rev. Biochem. 62:385–427, 1993.
Grant et al., "Overexpression of Multidrug Resistance–associated Protein (MRP) Increases Resistance to Natural Product Drugs", Cancer Research 54:357–361, Jan. 15, 1994.
Grynkiewicz et al., "A New Generation of $Ca^{2+}$ Indicators with Greatly Improved Fluorescence Properties", J. Biol. Chem. 260:3440–3450, 1985.
Hasmann et al., "Membrane Potential Differences between Adriamycin–sensitive and –Resistant Cells as Measured by Flow Cytometry", Biochem. Pharmacol. 38:305–312, 1989.
Haughland, R., "Handbook of Fluorescent Probes and Research Chemicals", Molecular Probes, Inc., Eugene OR, Larison K, Ed., pp. 163, 172–173, 1992.
Herweijer et al., "A Rapid and Sensitive Flow Cytometric Method for the Detection of Multidrug–Resistant Cells", Cytometry 10:463–468, 1989.

Hollo et al., "Calcein accumulation as a fluorometric functional assay of the multidrug transporter", Biochemica Biophysica Acta 1191:384–388, 1994.
Homolya et al., "Fluorescent Cellular Indicators Are extruded by the Multidrug Resistance Protein", The Journal of Biological Chemistry 268:21493–21496, Oct. 15, 1993.
Kessel et al., "Characterization of Multidrug Resistance by Fluorescent Dyes", Cancer Research 51:4665–4670, Sep. 1, 1991.
Konen et al., "The Multidrug Transporter: Rapid Modulation of Efflux Activity Monitored in Single Cells by the Morphologic Effects of Vinblastine and Daunomycin", J. Histochem. Cytochem. 37:1141–1145, 1989.
Mechetner et al., "Efficient inhibition of P–glycoprotein–mediated multidrug resistance with a monoclonal antibody", Proc. Natl. Acad. Sci. USA 89:5824–5828, Jul. 1992.
Neyfakh, A., "Use of Fluorescent Dyes as Molecular Probes for the Study of Multidrug Resistance", Experimental Cell Research 174:168–176, 1988.
Raviv et al., "Photosensitized Labeling of a Functional Multidrug Transporter in Living Drug–resistant Tumor Cells", J. Biol. Chem. 265:3975–3980, Mar. 5, 1990.
Sarkadi et al., "Expression of Human Multidrug Resistance cDNA in Insect Cells Generates a High Activity Drug–simulated Membrane ATPase", J. Biol. Chem. 267;4854–4858, Mar. 5, 1992.
Tanaka et al., "Use of Recombinant P–glycoprotein Fragments to Produce Antibodies to the Multidrug Transporter", Biochem. Biophys. Res. Com. 166:180–186, Jan. 15, 1990.
Wall et al., "Rapid Functional Assay for Multidrug Resistance in Human Tumor Cells Lines Using the Fluorescent Indicator Fluo–3", J. Natl. Cancer Int. 83:206–207, Feb. 6, 1991.
Wall et al., "Clinical Application of a Rapid, Functional Assay for Multidrug Resistance Based on Accumulation of the Fluorescent Dye, Fluo–3", Eur. J. Cancer 29A;1024–1027, 1993.
Yoshimura et al., "Novel screening method for agents that overcome classical multidrug resistance in a human cell line", Cancer Letters 50:45–51, 1990.

*Primary Examiner*—James C. Housel
*Assistant Examiner*—Jennifer Shaver
*Attorney, Agent, or Firm*—Allegra J. Helfenstein; Anton E. Skaugset

[57] ABSTRACT

The invention generally features a rapid, quantitative method of diagnosing multi-drug resistance in a patient. The method involves (a) exposing cells of a biological specimen to a calcein compound, the calcein compound becoming fluorescent in the cell; and (b) measuring calcein compound accumulating in the specimen cells relative to control cells, reduced calcein accumulation in specimen cells relative to control cells indicating the presence of multi-drug resistance in the biological specimen. The method is useful for diagnosing multi-drug resistance in patients undergoing drug therapy, e.g., chemotherapeutic or antibiotic therapy.

18 Claims, 10 Drawing Sheets

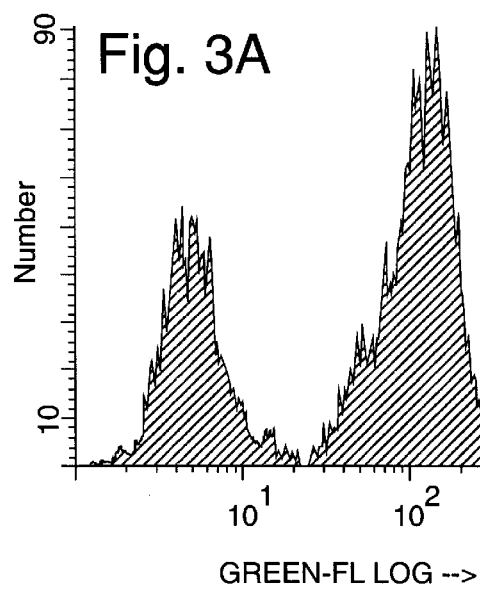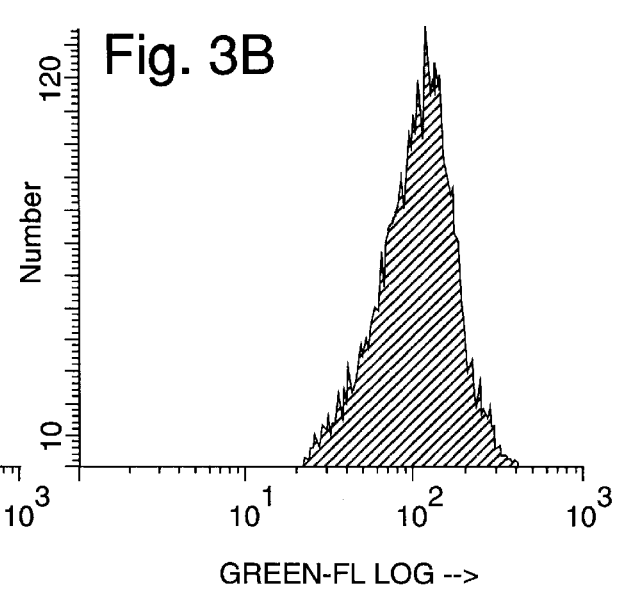

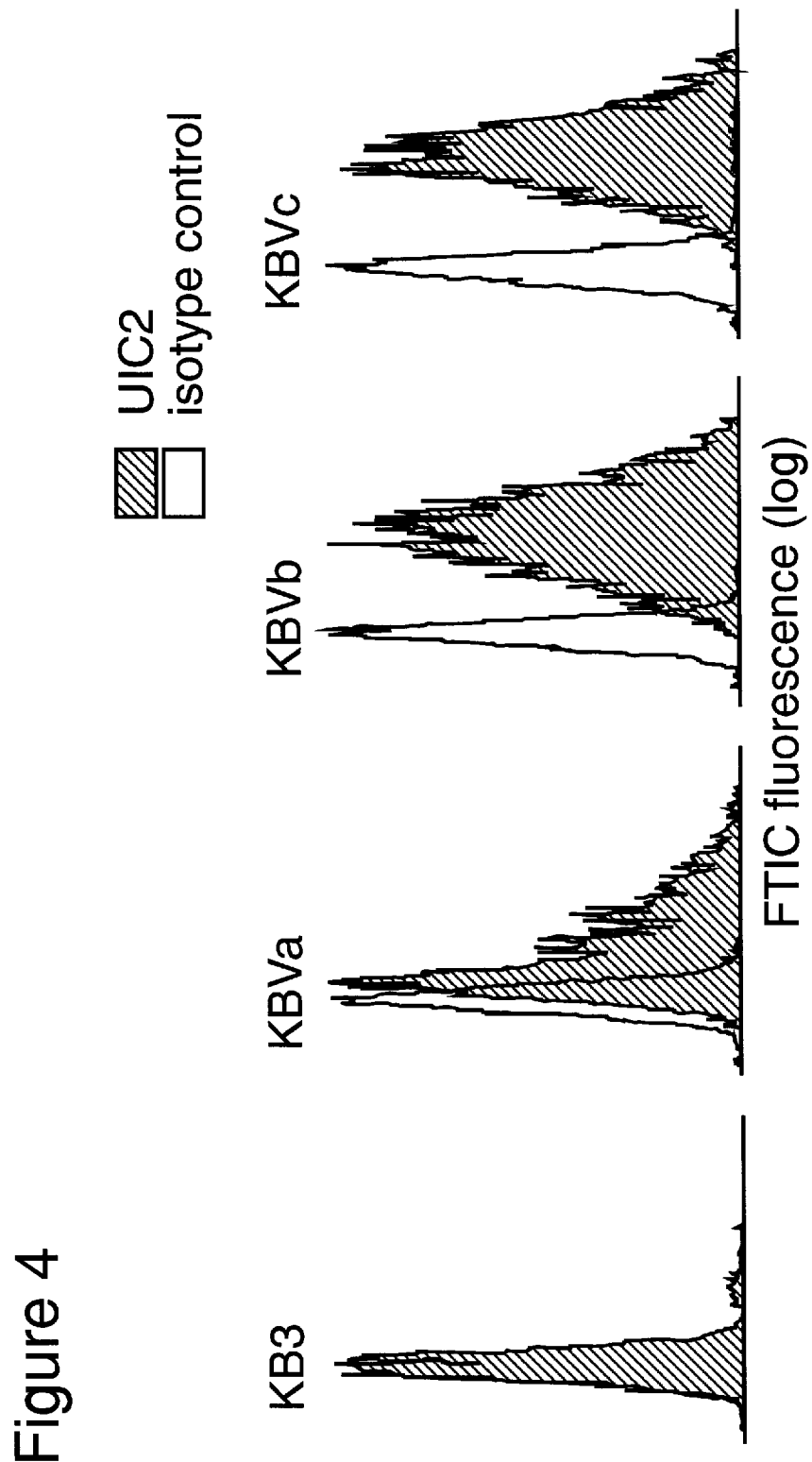

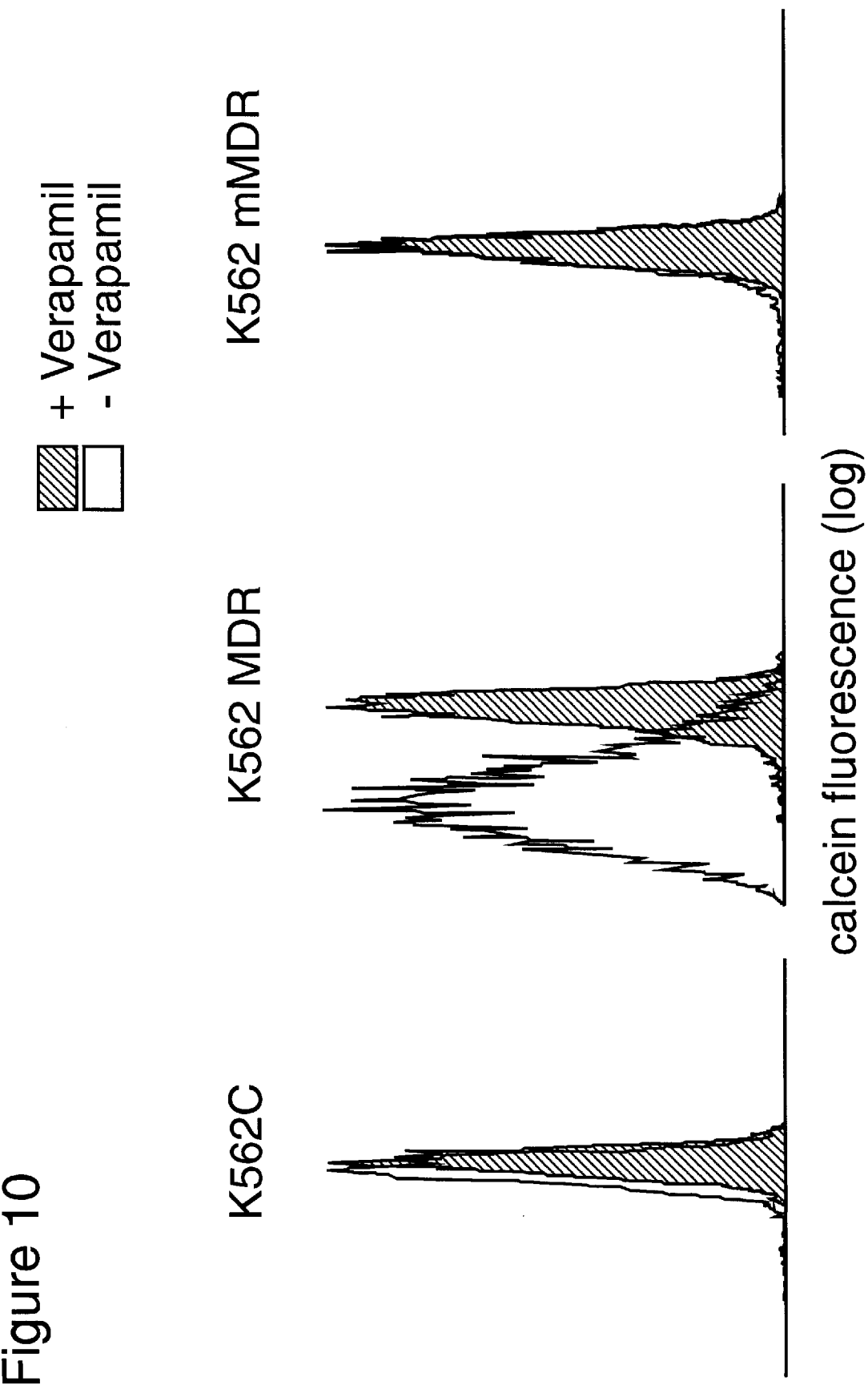

ASSAY FOR MULTI-DRUG RESISTANCE

This application is a continuation of application Ser. No. 08/322,702 filed on Oct. 13, 1994 now abandoned.

BACKGROUND OF THE INVENTION

This application bases priority on corresponding Hungarian application P94-02511, filed Aug. 31, 1994.

This invention relates to a diagnostic assay for the detection of multi-drug resistance.

Treatment of many diseases can be severely limited if the patient develops resistance to a chosen therapeutic drug. For example, chemotherapy, while generally an effective treatment against human cancerous diseases, is hampered when a patient becomes resistant to the chemotherapeutic. In one special form of drug resistance, called "Multi-drug Resistance," the patient's cells become resistant not only to the particular chemotherapeutic, but to a wide range of structurally and functionally unrelated drugs simultaneously (see Ford et al., *Pharmacological Reviews*, 42:155–199, 1992).

Multi-drug resistance is caused by an integral glycoprotein in the plasma membrane of the targeted cell. The most studied of these proteins is variously called Multi-Drug-Resistance 1 protein (MDR1), P-glycoprotein (pleiotropic-glycoprotein), Pgp, or P-170. Multi-drug resistance is also caused by a related homologue of MDR1, called the Multidrug-resistance Related protein (MRP)(Grant et al. *Cancer Res.* 54:357–361, 1994). The MDR1 and MRP proteins function as multi-drug transporters, catalyzing an energy dependent outward transport of drugs from the cell. They strongly resemble prokaryotic and eukaryotic members of the ABC (ATP Binding Cassette) transporters, or traffic ATPases (see Endicott et al., *Annu. Rev. Biochem.* 58:137–171, 1989; Higgins, *Annu. Rev. Cell. Biol.* 8:67–113, 1992).

MDR1 naturally functions to, and is highly expressed in tissues normally responsible for, extruding toxic materials and waste-products from cells (e.g., lung, kidney, and liver) and secreting hydrophobic compounds from exocrine or endocrine glands (Gottesman et al., *J. Biol. Chem.* 263:12163–12166, 1988; Higgins, *Annu. Rev. Cell. Biol.* 8:67–113, 1992). Consistent with its natural function, MDR1 catalyses an ATP-dependent extrusion of various cytotoxic drugs from the cell, e.g., vinca alkaloids, anthracyclines, and other natural antibiotics, thereby maintaining their cellular level at a subtoxic concentration. When expressed by tumor cells, MDR1 expels cytotoxic chemotherapeutic agents, and thus allows the tumor cell to survive anticancer treatments even at high drug doses. At the same time "ordinary" cells, having no such extrusion mechanism, may receive a lethal drug exposure. Tumors developing from tissues normally expressing MDR1 often show primary drug resistance, while in other tumors secondary drug resistance can develop during chemotherapy. A variety of agents have been proposed to reverse multi-drug resistance: e.g., verapamil, quinidine, calmodulin inhibitors, phenothiazines, reserpine, or cyclosporin A (Gottesman et al. *Annu. Rev. Biochem.* 62:385–427,1993).

In clinical treatment of various cancerous diseases reliable detection of multi-drug resistance would be extremely helpful. Combination chemotherapy treatment protocols could be adjusted and drug-resistance reversing agents could be applied accordingly.

In MDR1-expressing cells a decreased uptake of cytotoxic drugs can be visualized by measuring the cellular accumulation or uptake of fluorescent compounds, e.g., anthracyclines (Herweijer et al., *Cytometry* 10:463–468, 1989), verapamil-derivatives (Lelong et al., *Mol. Pharmacol.* 40:490–494, 1991), Rhodamine 123 (Neyfakh, *Exp. Cell Res.* 174:168–174, 1988); and Fluo-3 (Wall et al. *J. Natl. Cancer Inst.* 83:206–207, 1991; Wall et al. *Eur. J. Cancer* 29:1024–1027, 1993), respectively. However, quantitating cellular uptake of these fluorescence dyes may be difficult. For example, rhodamine 123 is poorly retained by the cells and interacts with various intracellular compartments and organelles, producing a spectral shift and a change in fluorescence intensity. Similarly, measurement of the steady-state distribution of fluorescent drugs or drug-mimicking compounds is made uncertain by the low sensitivity of the assay and the quenching effect of DNA and/or other cellular components.

SUMMARY OF THE INVENTION

The invention generally features a method of detecting multi-drug resistance in a biological specimen. The method involves (a) exposing cells of a biological specimen to a calcein compound; and (b) measuring the amount of calcein compound accumulating in the specimen cells relative to control cells, e.g., control cells lacking multi-drug resistance, or relative to cells with inhibited multi-drug resistant function. Reduced calcein accumulation in specimen cells relative to control cells indicates the presence of multi-drug resistance in the biological specimen.

"Multi-drug resistance", as used herein, refers to the ability of cells to develop resistance to a broad range of structurally or functionally unrelated drugs. Multi-drug resistance is recognized by those of skill in the art by its profile of cross-resistance (see, e.g., Gottesman et al. *Annu. Rev. Biochem.* 62:385–427, 1993; Riordan et al. *Pharmacol. Ther.* 28:51, 1985). Multi-drug resistance occurs by outward transport of the drug from the cell, the transport being mediated by a member of a family of multi-drug transporter proteins, which include MDR1 or a homologue of MDR1, e.g., Multi-drug Resistance Related Protein (MRP). Preferably, "multi-drug resistance" refers to the state which is dependant on expression or overexpression of MDR1, MRP, or a related homologue, and/or on amplification of a gene encoding a multi-drug transporter protein, e.g., human mdr1. A "homologue of MDR1", as used herein, is a protein whose expression causes the cross-resistance profile described above, and has common evolutionary origin with MDR1, e.g., by being functionally and structurally related to the family of ABC transporter proteins, (for an analysis of the structural similarity of MDR1-related proteins see, e.g., Cole et al., (*Science* 258:1650–1654, 1992) and/or Juranka et al. (*FASEB Jour.* 3:2583–2591, 1989).

Multi-drug resistance includes both primary and secondary multi-drug resistance. Where the drug resistance is "primary" the cell has experienced no previous exposure to a member of the group of drugs, yet exhibits inherent resistance to them. Where drug resistance is "secondary", the cell has been exposed to only one drug, or to only a subset of two or more, but not necessarily to the whole, group of drugs affected by resistance.

A "calcein compound", as used herein, refers to a derivative of calcein with the properties, e.g., of being a substrate to a multi-drug transporter protein; being permeable to cell membranes, so as to diffuse through the extracellular membrane and enter a cell; and having low sensitivity to $Ca^{2+}$ ions, $Mg^{2+}$ ions, and pH. Once inside the cell the side groups of the calcein compound derivative are cleaved by intracellular esterase activity, resulting in a charged non-membrane permeable form of calcein, hereafter referred to as "free calcein". The calcein compound derivative is colorless and nonfluorescent until hydrolyzed, becoming fluorescent in its non-membrane permeable hydrolyzed form. Calcein compound derivatives include, but are not limited to, acetoxymethyl esters of calcein, e.g., calcein-AM, calcein blue AM, or carboxycalcein blue AM, or an acetate ester of calcein (see, e.g., Haughland et al., eds. *Handbook of Fluorescent Probes and Research Chemicals,* 5th ed. 1992–1994, Molecular Probes, Eugene Oreg.).

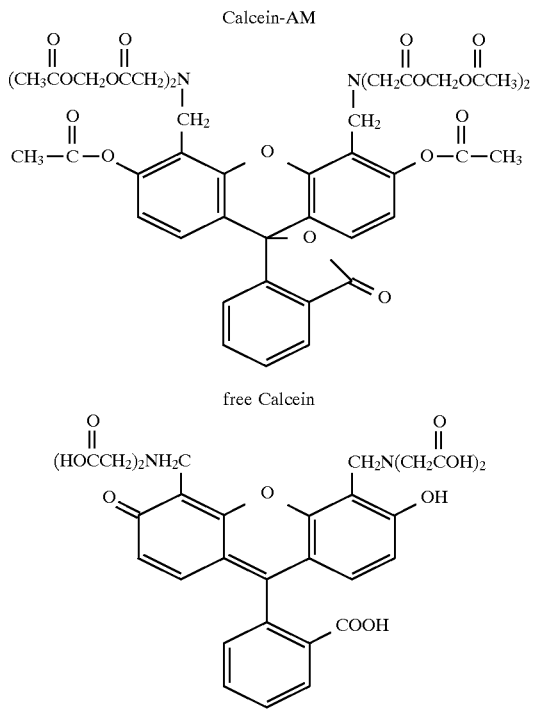

By "measuring calcein compound" is meant determining the amount of the calcein compound which accumulates in a cell as an inverse indication of the amount of calcein extruded from the cell by a multi-drug transporter protein. Techniques for measuring intracellular calcein include, but are not limited to, flow cytometry, fluorimetry, or cell imaging. Use of calcein as a fluorescent probe, in combination with these techniques, provides a quantitative, functional assay of MDR1 activity. By "exposing" is meant placing the calcein compound in the environment of the cells of the biological specimen, e.g., by adding the calcein compound to the media in which the cells of the biological specimen are incubated, so as to allow the calcein compound to enter the cells.

In one embodiment of the method of detecting multi-drug resistance in a biological sample, the control cells can be a portion of the biological sample itself, the method further including exposing the control cells to an inhibitor of multi-drug resistance. The experimental and control cells are each portions of the same biological sample, or are within the same portion of the biological sample, to which an inhibitor of multi-drug resistance is added at a later time in the incubation (see FIG. 1B, curve C). By using portions of the same biological sample, or by controlling the temporal sequence by which the components are added, the control acts as an internal, or "self", control. As used herein, "an inhibitor of multi-drug resistance" refers to a compound which inhibits multi-drug resistant-dependent calcein compound extrusion either competitively or noncompetitively. Such compounds, which are known to those skilled in the art, preferably include vinblastine, and also include, but are not limited to, e.g., verapamil, vincristine, oligomycin, or cyclosporin. Other multi-drug resistance-inhibitors useful in the invention include any of the Reversin compounds described in the Patent Cooperation Treaty Application PCT/IB94/00144 (hereby incorporated by reference). Additional multi-drug resistance inhibitors are known to those of skill in the art, or can be identified by the methods demonstrated herein.

In a related embodiment, the method of the invention can further include a step of determining the amount of a multi-drug transporter protein made by the cells of the biological specimen. The amount of multi-drug transporter protein, e.g., MDR1 or MRP, made or expressed by the cell, or the amount of multi-drug transporter protein RNA message transcribed by the cell, can be determined by methods known to those of skill in the art. For example, a technique for measuring the expression of a multi-drug transporter protein includes immunoblotting, e.g., by Western blotting. A technique for quantifying the amount of message in cellular RNA that encodes a multi-drug transporter protein is, e.g., Northern blotting. A technique for determining the amount of multi-drug transporter protein on the surface of a cell of the biological specimen includes, e.g., flow cytometry.

By a "biological specimen", or a "biological sample", is meant a sample of living cells or tissue from a mammal. The biological specimen can be isolated from the mammal as a tissue sample, e.g., a biopsy sample, as a body fluid, e.g., blood or plasma, or as a cellular swab. Preferred cells include any living cell that has potentially developed multi-drug resistance and is the target of a therapeutic compound, including, but not limited to, white blood cells, cancerous cells, cells from endothelial or epithelial layers, or cells from lymphoid organs.

In another related aspect the invention features a kit that includes instructions for carrying out a method of detecting multi-drug resistance in a biological specimen that involves use of a calcein probe. The instructions provide any or all of the aspects of one of the various methods of the invention. The kit can further include a calcein compound derivative described above. The kit can also further include an inhibitor of multi-drug resistance. By "kit" is meant a package, collection, or container of materials intended to aid one in use of the assay of the invention. By "instructions" is meant a list of steps, or a description of the invention, intended to instruct a practitioner, e.g., a laboratory clinician or technician, to conduct an assay of the invention. The instructions can be written, oral (e.g., on an audio tape medium), or visual (e.g., on a video tape medium).

The method of the invention is useful for the diagnosis of multi-drug resistance in a mammal, e.g., a human, or a domesticated animal, e.g., an agricultural animal, a laboratory animal, or a protected animal, e.g., a zoo animal, or any animal that potentially exhibits resistance against a therapeutic compound. Therapeutic compounds include, but are not limited to, a chemotherapeutic, antiparasitic, or antibiotic compound. As used herein, a "therapeutic compound", or a "drug", includes a medication, a pharmaceutical, or a substance which is intended for use in diagnosis, cure, mitigation, treatment, or prevention of disease, or which is generally intended to affect the structure or the function of the body of an animal. A "chemotherapeutic drug" includes any drug intended to target and kill a tumor cell, e.g., a neoplastic, malignant, or benign tumor cell, in a mammal. An "antiparasitic drug" includes a drug intended to target the agent of a parasitic infection, e.g., ascaris, enterobium, hookworm, threadworm, tapeworm, schistosomes, whipworm, protozoa, e.g., intestinal or extraintestinal amebas, giardia, malaria, toxoplasma, or trichomonas. An "antibiotic drug" includes substances which inhibit or kill fungal or bacterial microorganisms, e.g., actinomycin. Examples of drugs within the scope of the invention include, but are not limited to, any chemotherapeutic, antiparasitic, and antibiotic drugs which clinically elicit, or whose therapeutic effects are limited by, primary or secondary multi-drug resistance caused by MDR1 (Ford et al. supra; hereby incorporated by reference).

Other features and advantages of the invention will be apparent from the following detailed description and from the claims.

DETAILED DESCRIPTION

We first briefly describe the drawings.

Drawings

FIG. 3 is an illustration of the use of flow cytometry and calcein accumulation to detect MDR1 function in a mixed population of control and MDR1-transfected NIH 3T3 fibroblasts.

FIG. 4 is a plot showing the cell surface expression of MDR1 measured by flow cytometry.

FIG. 10 is a plot showing flow cytometry measurements of calcein accumulation in K562 control cells, K562 drug resistant cells (MDR), and K562 cells expressing a mutant MDR1 protein (mMDR).

Figure 1:
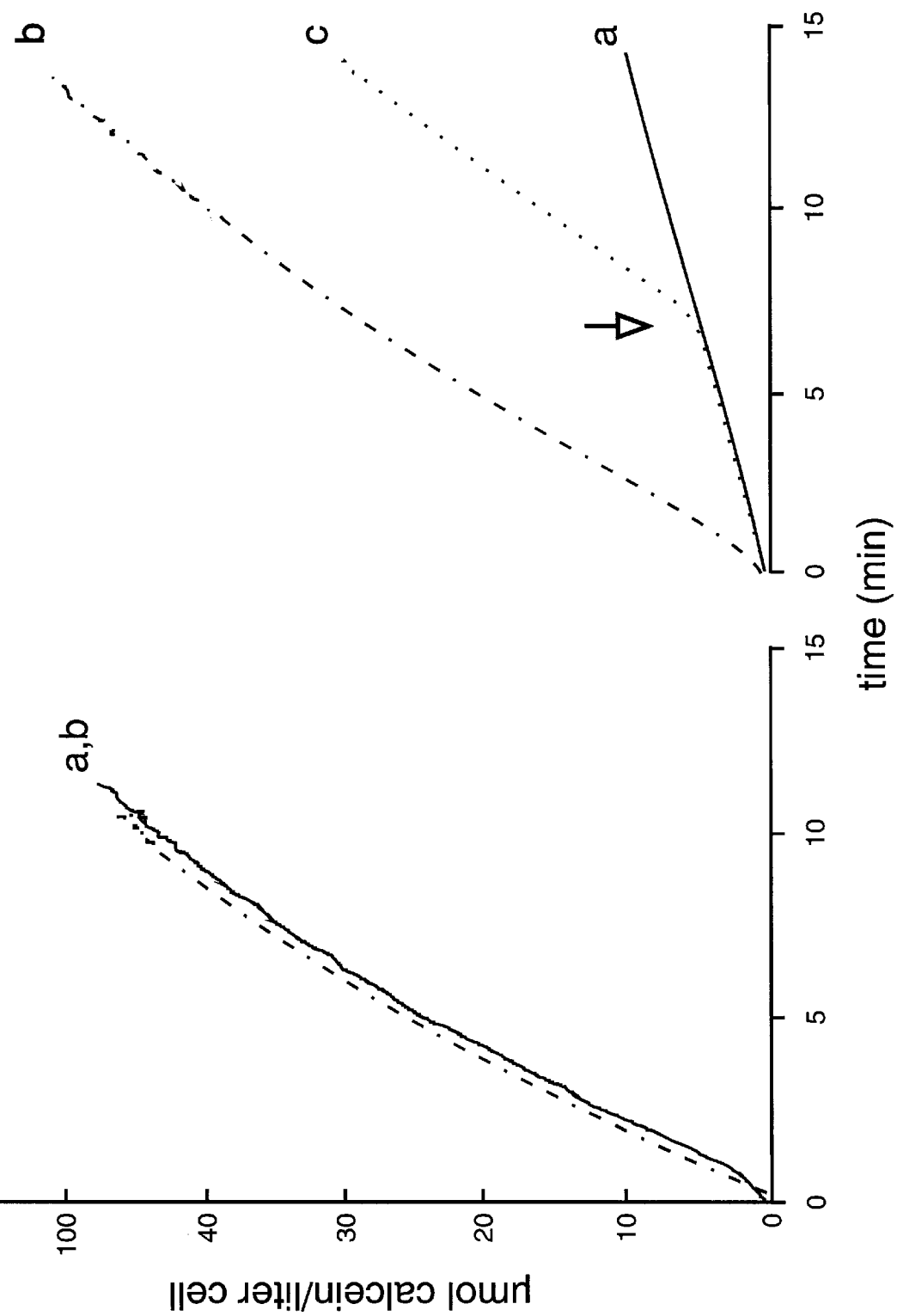
FIG. 1A is a graphical representation of a time course of calcein accumulation in control NIH 3T3 fibroblasts.
FIG. 1B is a graphical illustration of a time course of calcein accumulation in MDR1-transfected NIH 3T3 fibroblasts.

Applicants have shown that the hydrophobic acetoxymethyl ester (AM) derivative of the fluorescent indicator calcein is actively extruded from cells by the multi-drug transporter proteins MDR1 and MRP, making it an excellent probe for functionally detecting multi-drug resistance. Using a calcein derivative as described above, e.g., calcein-AM, has advantages over using other fluorescent dyes (e.g., fura-2, fluo-3, indo-1, quin-2, and BCECF (2'7'-bis(2-carboxyethyl)-5(6)-carboxyfluorescein). Calcein-AM is highly lipid soluble, rapidly penetrates the plasma membrane of cells, and is practically non-florescent. By cleaving the ester bonds, intracellular esterases transform calcein-AM to a hydrophilic and intensively fluorescent free acid form. Calcein-AM (but not free calcein) is an excellent activator of the MDR1-ATPase in isolated membranes ($K_a \geq 1$ $\mu$M), and its accumulation is prevented in MDR1-expressing cells. Moreover, the calcein-AM dye does not show significant binding to cellular components. Free calcein has a high molar emission coefficient (about 7.5-fold higher than that of Fura-2), with no apparent cytotoxicity. It accumulates efficiently in the cells ($T_{1/2}$ of calcein leakage is about 3 hours at 37° C.), with fluorescence essentially insensitive to changes in pH, $Ca^{2+}$ or $Mg^{2+}$ (Haughland et al. supra). Calcein-AM is extruded by MDR1 before its intracellular conversion to the non-MDR1 substrate free calcein (Homolya et al. *J. Biol. Chem.* 268:21493–21496, 1993; Holló et al. *Biochem. Biophys. Acta.* 1191:384–388, 1994). The fluorescence excitation and emission maxima of calcein are 496 and 517 nm, respectively, making this dye suitable for both conventional fluorescence/flow cytometric and laser-scanning microscopic applications. When calcein-AM extrusion is blocked by an agent which interferes with the MDR1 pump (e.g., verapamil), the fluorescent dye form rapidly accumulates. Since calcein has a high fluorescence intensity and its accumulation during a few minutes of incubation may produce intracellular free dye concentrations 100–500 fold of that of calcein-AM in the medium, the assay is highly sensitive.

Applicants have enhanced the sensitivity and reliability of the calcein multi-drug resistance assay provided herein for clinical use by providing a quantitative measure of MDR1 function, in the form of the activity factor (f) described below.

EXAMPLE 1

Methods

Cell Culturing:

P388 murine leukemia, F4–6 Friend murine erythroleukemia, K562 human erythroleukemia, KB3 and KB-V1 human epidermoid carcinoma cells were cultured under standard conditions in RPMI or DMEM media containing 10% fetal bovine serum, 5 mM glutamine, 100 units/ml penicillin, and 100 $\mu$/ml streptomycin. All of these cell lines had parent (non-resistant), and drug-selected, multi-drug-resistant counterparts. Resistant cell lines were selected by various concentrations of cytostatic agents to achieve different levels of drug-resistance. P388 and K562 cells were grown in media containing 50 ng/ml and 100 ng/ml adriamycin, respectively. KB-V cells were cultured in 50–500 ng/ml vincristine containing media. In order to achieve different levels of drug-resistance the selection procedure was repeated several times.

NIH 3T3 fibroblasts were cultured under standard conditions in Dulbecco's modified Eagle's medium (DMEM) containing 10% fetal bovine serum, 5 mM glutamine, 100 units/ml penicillin, and 100 $\mu$g/ml streptomycin, as described by Homolya et al. (supra). MDR1-transfected cells (NIH 3T3 MDRI G185) were prepared and characterized for drug-resistance as described (Bruggemann et al., *J. Biol. Chem.* 267:21020–21026, 1992). Recombinant baculovirus carrying the human MDRI gene was generated, and the Sf9 (*Spodoptera frugiperda*) cells were infected by the MDR1-baculovirus and cultured according to standard procedures (Germann et al. *Biochemistry* 29:2295–2303, 1990).

Quantitative immunoblotting:

Electrophoresis and immunoblotting with the 4077 polyclonal antibody, which recognizes both mouse and human MDR1 (Tanaka et al., supra), were carried out as described in Sarkadi et al., (*J. Biol. Chem.* 267:4854–4858, 1992). The second antibody was an anti-rabbit, peroxidase (HRP)-conjugated goat IgG (Jackson Immunoresearch), used in 20,000× dilutions. HRP-dependent luminescence on the PVDF membrane immunoblots (ECL, Amersham) was determined by excising the respective bands from the PVDF membrane and measuring their luminescence in a liquid scintillation counter (Beckman LS 6000, Single Photon Monitor mode). The amounts of the expressed MDR1 were calculated from luminescence values, based on a calibration by a dilution series of standard Sf9-MDR1 membrane preparations. By using this method a wide range of luminescence intensities (over three orders of magnitude) could be detected with high accuracy.

RNA Northern blotting:

Total cellular RNA was isolated by the acid guanidinium thiocyanate-phenol-chloroform method (Chomczynski et al., *Anal. Biochem.* 162:156–159, 1987). Electrophoresis and Northern blotting were carried out as described in Schaefer et al., (*J. Biol. Chem.* 268:10876–10880, 1993). In particular, 30 μg samples of RNA were denatured by glyoxylation, size-separated by electrophoresis through 1.5% agarose, transferred to Biodyne A membrane by capillary blotting using 20× standard saline citrate solution (SSC), and immobilized by baking the membrane at 80° C. for 1.5 h. The cDNA hybridization probes (1.2 kb PstI fragment of human β-actin, plasmid cDNA of human MDR1) were labeled with ($\alpha$-$^{32}$P) dCTP by a random primer method. Membrane prehybridization (six hours) and hybridization (18 hours) were carried out at 42° C. in standard hybridization media containing 50% formamide.

Fluorometry:

Calcein uptake was measured by incubating $2.5 \times 10^5$ cells/ml in HPMI medium (120 mM NaCl, 6 mM KCl, 0.1 mM $MgCl_2$, 0.01 mM $CaCl_2$, 10 mM HEPES.Na (pH 7.4), 10 mM $NaHCO_3$, 10 mM glucose, and 5 mM $Na_2HPO_4$; Homolya et al., supra) containing 0.25 μM calcein-AM (Molecular Probes, Eugene, Oreg.). Fluorescence was measured at 37° C. with rapid stirring in a Hitachi F-4000 fluorescence spectrophotometer (excitation and emission wavelengths for calcein were 493 nd 515 nm, respectively, with a band width of 5 nm). Calibration of dye concentration was based in the measurement of free calcein fluorescence in the same instrument under identical conditions. All experiments were repeated at least three times with each batch of cell preparation.

Flow cytometry:

For immunofluorescence staining $3 \times 10^5$ cells were resuspended in HPMI+1% bovine serum albumin (BSA) medium containing the monoclonal antibody UIC2 (10 μg/ml), which reacts with extracellular epitope(s) of the MDR1 protein (Mechetner et al., supra). Labeling was performed at 4° C. for 45 minutes, and the cells were then washed twice with HPMI containing 1% BSA, and once with HPMI. Thereafter an anti-mouse-FITC antibody conjugate (DAKO 17 μg/ml) was applied similarly to the first antibody. Finally the cells were resuspended in HPMI. Cellular fluorescence was measured with a Cytoronabsolute™ flow cytometer (Ortho Diagnostics System, N.J.).

For flow cytometry measurements of calcein uptake, $2 \times 10^5$ cells/ml were incubated to 10 minutes at 37° C. in HPMI, containing 0.25 μM calcein-AM. During a preincubation period, when indicated, verapamil (100 μM) was applied for 5 minutes at 25° C. To eliminate non-living cells the samples were stained with propidium iodide, which stains the nuclei of non-living cells red. Cells with red nuclei were thereby detected and gated out. Further fluorescent measurements were limited to green fluorescence. Data were analyzed by the Winlist software (Verity Software House, Inc.).

Single Cell Imaging:

The accumulation of calcein by cells can be monitored by photographing single cell images, e.g., of a histological specimen. Cells can be grown on coverslips, e.g., for two days, and then incubated in an HPMI bath containing 1 μM calcein-AM. Cellular fluorescence is monitored with a fluorescence imaging system, e.g., a Zeiss IM-35 invert microscope (Nikon 100/1.3 CF-Fluor objective). The cells are photographed using, e.g., a Dage 72 CCD camera, and a DAGE GenIISys intensifier.

Calculations and Modeling:

During calcein accumulation measurements the increase in fluorescence depends on various parameters (e.g. emission coefficient, cell volume, cell number, dye concentration, esterase activity). In order to obtain a parameter which reflects solely the MDR activity, the dye uptake rate was normalized to an internal standard. Thus dye accumulation was also measured in the presence of an MDR inhibitor (e.g. verapamil), and the dye uptake was expressed by the following dimensionless parameter:

$$F = \frac{(F^* - F)}{F^*} \tag{1}$$

where F* and F designate the dye accumulation rate in the presence and absence of the inhibitor, respectively. In order to understand the behavior of this parameter, a mathematical model has been constructed. This model was based on simple first order kinetics and its principle is summarized on the following scheme:

SCHEME 1

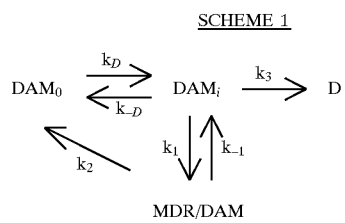

MDR/DAM where $[DAM]_o$ designates the dye AM concentration in the incubation medium, and $[DAM]_i$ means the dye AM concentration at the point where the multi-drug transporter binds its substrate. [MDR/DAM] designates the MDR-substrate complex, and [D] is the concentration of the free acid form of the dye. The rate constants are indicated by $k_i$ where the indices are referring to the different steps in the process. The first step is the diffusion of dye AM into the cell ($k_D$, $k_{-D}$), which is followed by the formation of the MDR-substrate complex (($k_1$, $k_{-1}$), and by the MDR dependent transport step ($k_2$). In addition to this process, a part of dye AM gets into the cytoplasm, where it is cleaved by non-specific esterases. Though the latter process probably consists of more steps, it is described with a single first-order reaction ($k_3$). The time courses of the concentrations of the key components are described by the following equations:

$$\frac{d[DAM]_i}{dt} = k_D[DAM]_o - k_{-D}[DAM]_i - k_1[MDR][DAM]_i + \tag{2}$$

$$k_{-1}[MDR/DAM] - k_3[DAM].$$

-continued $$\frac{d[MDR/DAM]}{dt} = \quad (3)$$

$$k_1[MDR][DAM]_i - k_{-1}[MDR/DAM] - k_2[MDR/DAM]$$

$$\frac{d[D]}{dt} = k_3[DAM]_i \quad (4)$$

The model includes the following assumptions and considerations: 1) transport by MDR1 is described by Michaelis-Menten kinetics; 2) the free acid form of the dye is not transported by MDR1 (Homolya et al., supra); 3) the concentrations of $[DAM]_i$ and $[MDR/DAM]$ are in steady state; 4) esterase cleavage is described by a single first order reaction; 5) $[DAM]_o$ is considered constant, since the external volume is much larger than the total volume of cells; and 6) the applied inhibitor entirely eliminates dye transport by MDR1.

Considering the latter assumption, in the presence of the inhibitor the model can be simplified as follows:

SCHEME 2

$$DAM_0 \underset{k_{-D}}{\overset{k_D}{\rightleftarrows}} DAM_i \xrightarrow{k_3} D$$

$$\frac{d[DAM]_i^*}{dt} = k_D[DAM]_o - k_{-D}[DAM]_i^* - k_3[DAM]_i^* \quad (5)$$

$$\frac{d[D]^*}{dt} = k_3[DAM]_i^* \quad (6)$$

where the asterisk is referring to concentrations in the presence inhibitor. Considering the steady state assumption, the dye uptake rate in the presence of inhibitor can be expressed as:

$$\frac{d[D]^*}{dt} = K_e k_D [DAM]_o \quad (7)$$

where $K_e$ designates $k_3/(k_{-D}+k_3)$, which is equal to unity if we disregard back-diffusion. In steady state, equations (2) and (3) are equal to zero. The dye uptake rate in the absence of inhibitor can be expressed as follows:

$$\frac{d[D]}{dt} = \frac{1}{2}\left[ K_e k_D[DAM]_o - k_3 K_m - K_e v_{max} + \sqrt{(K_e k_D[DAM]_o - k_3 K_m - K_e v_{max})^2 + 4 k_3 K_m k_D [DAM]_o} \right] \quad (8)$$

where $K_m$ and $v_{max}$ are the Michaelis constant and the maximum transport rate of MDR1, respectively. Combining equations (1), (7), and (8), the f parameter can be expressed as

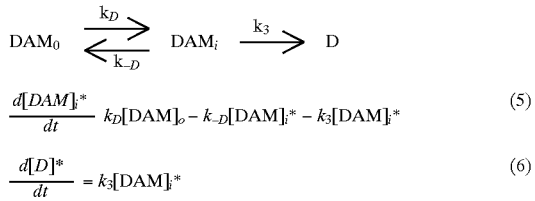

where $a=1/(k_D[DAM]_o)$ and $b=k_3 K_m/K_e$. Equation (9) provides a direct connection between f and $v_{max}$, since parameters a and b are constant. When examining the behavior of this model, f appears to be independent from $K_e$ and monotonously increasing with $v_{max}$. For this latter reason f will subsequently be referred to as the "MDR activity factor". At low levels of MDR1 expression, f is nearly proportional to $v_{max}$ (see FIG. 10), and the slope of its asymptote is equal to a. In contrast, at high MDR levels f converges to 1. Therefore the sensitivity of the MDR activity factor is higher at the low MDR expression levels, thus it provides a suitable measure of MDR activity probably in the range of clinical interest.

EXAMPLE 2

Demonstration of Calcein Extrusion by MDR1

In the experiments shown in FIG. 1A and FIG. 1B, calcein accumulation was measured in a spectrofluorometer using control NIH 3T3 fibroblasts and NIH 3T3 fibroblasts that were stably expressing human MDR1. Cells were incubated with 0.25 μM calcein-AM in HPMI at 37° C. The concentration of accumulated calcein was plotted against time. In each of FIGS. 1A and 1B, curve a represents calcein accumulation without verapamil addition; curve b represents preincubation with verapamil (40 μM) for 5 minutes before beginning the loading period. To generate curve c (FIG. 1B), verapamil (40 μM) was added to MDR1-expressing cells at the time indicated by the arrow. The mean volume of control and MDR1-expressing NIH 3T3 cells was estimated in a Coulter Channelizer to be 1000 fl/cell.

When the cells were incubated in the presence of verapamil, MDR1-expressing fibroblasts showed an approximately 6–8 times lower rate of calcein accumulation than the control cells (curve a, FIGS. 1A and 1B). Preincubation of the cells with verapamil, an effective MDR1-reversing agent (Tsuruo et al., Cancer Res. 41:1967–1972, 1981), restored the rate of dye accumulation in the MDR1 cells almost to the control level (FIG. 1B, curve b), and the addition of verapamil during calcein dye loading produced a similar increase in dye accumulation (FIG. 1B, curve c). In contrast, verapamil had no effect on calcein accumulation in the control NIH 3T3 cells (FIG. 1A, Curve b). After washing and resuspending the cells in calcein-free medium, no calcein was observed to leak into the medium over a period of 180 minutes from either control or MDR1 cells. Addition of verapamil had no effect on calcein accumulation in either cell type. Calcein trapping properties are not influenced by changes in extracellular pH between 7.0 and 7.8. These experiments suggest that calcein efficiently accumulates in the cells and is not exported by the multi-drug transporter. In addition, immunoblot experiments with 4077 MDR1-specific polyclonal antibody demonstrate the presence of large amounts of the 170 kDa MDR1 in MDR1-transfected fibroblasts.

EXAMPLE 3

Effect of MDR1 Inhibitors on Calcein Accumulation

The effects of various inhibitors and substrates of the multi-drug transporter on calcein accumulation in control and MDR1-expressing NIH 3T3 cells were determined (Table 1). The inhibitors and substrates included, e.g., verapamil, vinblastine, oligomycin, cyclosporin A, and UIC2 (an inhibitory monoclonal antibody). As shown above (FIGS. 1A and 1B), verapamil increased calcein accumulation in the MDR1 fibroblasts without any effect on the control cells. Vinblastine, a well-known drug substrate of MDR1 (Horio et al., Proc. Natl. Acad. Sci. USA 85:3580–3584, 1988), increased calcein trapping in the MDR1 fibroblasts, probably by competing with the MDR1 transporter, while no significant effect could be observed in the control cells. Cyclosporin A, an effective drug-resistance reversing agent (Slater et al., J. Clin. Invest. 77:1405–1408, 1986) and oligomycin, a potent inhibitor of MDR1-mediated drug transport (Horio et al., supra) and MDR1-ATPase activity (Sarkadi et al., *J. Biol. Chem.* 267:4854–4858, 1992; and Ambudkar et al., *Proc. Natl. Acad. Sci. USA* 89:8472–8476, 1992), also restored dye accumulation almost to the control level, although the latter slightly inhibited calcein accumulation in the control fibroblasts as well. The UIC2 monoclonal antibody, which recognizes extracellular epitopes of MDR1 and inhibits drug transport (Mechetner et al., *Proc. Natl. Acad. Sci. USA* 89:5824–5828, 1992) increased calcein accumulation by almost 50% in the MDR1 fibroblasts, without any effect on the control cells.

TABLE 1

Effects of various inhibitors of multi-drug resistance on calcein accumulation in NIH 3T3 fibroblasts

| Treatment | Calcein Accumulation ($\mu$mol/min per liter of cells) | |
| --- | --- | --- |
| | control cells | MDR1 cells |
| None | 3.56 ± 0.51 | 0.63 ± 0.26 |
| Verapamil (40 $\mu$M) | 3.53 ± 0.70 | 3.80 ± 0.79 |
| Vinblastine (50 $\mu$M) | 3.60 ± 0.63 | 4.03 ± 1.10 |
| Oligomycin (30 $\mu$M) | 2.46 ± 2.46 | 2.83 ± 0.11 |
| UIC2 (30 $\mu$g/ml) | 3.55 ± 0.55 | 1.99 ± 0.35 |
| Cyclosporin A (5 $\mu$M) | 3.54 ± 0.42 | 3.84 ± 0.61 |

Calcein accumulation rate was expressed as $\mu$mol free calcein/min liter of cells, ± S.E. (n = 3)

EXAMPLE 4

Flow Cytometric Detection of Multi-Drug Transporter Function

Figure 2:
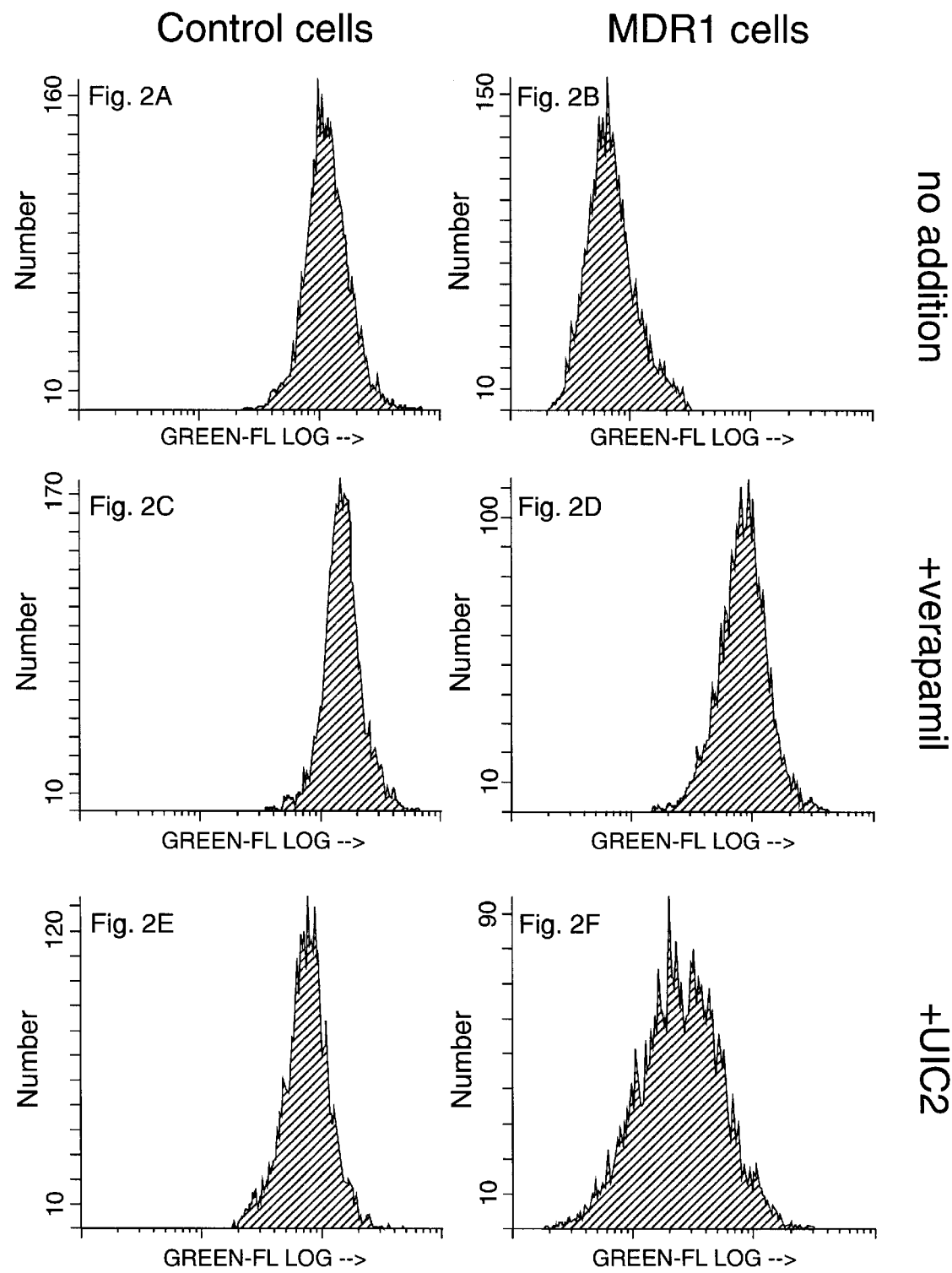
FIG. 2 is an illustration of the use of flow cytometry and calcein accumulation to detect MDR1 function in control versus MDR1-transfected NIH 3T3 fibroblasts.

Flow cytometric measurements were carried out to determine whether the kinetic differences in calcein accumulation seen in the spectrofluorometric experiments (FIGS. 1A and 1B) allow a discrimination between MDR1 and control cell population under quasi-steady-state loading conditions. FIG. 2 shows representative data of calcein loading experiments in control (FIGS. 2A, 2C and 2E) and MDR1-transfected (FIGS. 2B, 2D and 2F) cells. After preincubation at 25° C. with the inhibitors (FIGS. 2A, and 2B: no addition; FIGS. 2C, 2D: verapamil 40 $\mu$M for 6 minutes; FIGS. 2E, 2F: UIC2 Mab, 10 $\mu$g/ml for 30 minutes) $10^5$ cells/ml were further incubated in the calcein-AM (0.25 $\mu$M) containing medium at 37° C. for 15 minutes. Green fluorescence intensity was measured. Data are shown as numbers of cells plotted against the log fluorescence intensity.

The accumulation of calcein in a mixed population of control and MDR1-transfected cells was measured in the absence (FIG. 3A) and presence (FIG. 3B) of verapamil (FIG. 3), by the same techniques used for the experiment shown in FIG. 2.

This experiment demonstrated that after a 15 minute incubation of the cells with calcein-AM, MDR1-expressing NIH 3T3 cells accumulated much smaller amounts of calcein than the control cells. Pretreatment with verapamil or the UIC2 inhibitory antibody resulted in increased calcein accumulation in the MDR fibroblast population, without having any significant effect on dye accumulation in the control cells (FIG. 2). MDR1 expressing and drug-sensitive cell-mixing experiments showed a clear distinction between the two cell populations on the basis of their calcein fluorescence, while the addition of verapamil caused a significant fluorescence shift to high intensity levels affecting only the MDR1 cell population (FIG. 3).

EXAMPLE 5

Quantitative Detection of MDR1 Expression by Western Blotting, Northern Blotting, and Flow Cytometry Immunofluorescence Applicants aim was to establish a correlation between the expression level of the MDR1 protein and its functional consequence, the resistance to cytotoxic agents in a wide variety of cell types. Therefore MDR1 expression was measured in mouse P388 leukemia and Friend erythroleukemia (F4–6) cell lines, as well as human epidermoid carcinoma (KB) and erythroleukemia (K562) cells, all of which had parent, non-resistant, and drug-selected, multi-drug-resistant counterparts. Moreover, by continuous selection, a great variety of the levels of drug-resistance were achieved in all these cell types. As a control, NIH 3T3 mouse fibroblasts and cells from the same cell line stably transfected with the human MDR1 cDNA via a retroviral vector were used (Bruggemann et al., supra). For the quantitative estimation of the MDR1 protein on the immunoblots, we used the insect (Sf9) cell expression system (Germann et al., supra).

Western blot detection of the multi-drug resistance protein in TCA-precipitated protein extracts of NIH 3T3 cells (Lane 1=control, lane 2=MDR1-transfected), of P388 mouse leukemia cells (lane 3=control; lanes 4 and 5: P388 cells selected by adriamycin, and expressing low ($MDR_a$) and high ($MDR_b$) amounts of MDR1, respectively), and of human MDR1-expressing Sf9 cell membranes (lane 6). Western blots showed increasing amounts of MDR1 protein in a series of human epidermoid carcinoma (KB) cell lines (lane 1=KB3 control cells; lanes 2–4 are vincristine-selected KBV1 cells expressing low ($KBV1_a$), intermediate ($KBV1_b$) and high ($KBV1_c$) amounts of MDR1). Luminograms of the peroxidase-stained blots (described above) were prepared, where each lane contained 20 $\mu$g of cellular protein, with the exception of lane 6, which contained 2 $\mu$g of protein from MDR1-expressing Sf9 insect cell membranes. Full electroblot transfer of the large, heavily glycosylated MDR protein to PVDF membranes was performed according to the method of Sarkadi et al. (supra). An anti-human MDR1 polyclonal antibody (4077) was used which recognizes mouse MDR1 but does not show cross-reaction with MDR2 (Tanaka et al., supra) with any other cellular protein.

The immunoreactive bands represent the human MDR1 protein, its glycosylated form running at an apparent $M_r$ of approximately 170 kDa, while the underglycosylated form expressed in Sf9 cells at an $M_r$ of about 130 kDa. The mouse MDR1 (with an $M_r$ of about 160 kDa) in the P388 cells is detected with the same antibody. Based on the quantitative luminescence measurements (see Methods), and the known amount of the MDR1 protein in the Sf9 membranes (30 $\mu$g/mg membrane protein [Sarkadi et al., supra]), the MDR1 expression levels in the different cell lines could be determined. The mean values obtained in at least three different measurements for the various cell lines were calculated. In the case of the mouse MDR1, antibody detection may be less efficient, thus an underestimation of the amount of MDR1 may occur. However, the validity of these measurements is supported by the finding that another polyclonal anti-human MDR1 antibody (4007, prepared against the C-terminal cytoplasmic domain [Tanaka et al., supra]) provided a similar value for MDR1 expression in all cell types examined.

Northern blotting of the RNA extracted from the drug-resistant ($KB-V1_b$, and $KB-V1_c$) and control (KB3) cells, respectively shows that bands at 4.5 kbase represent the MDR1 message, while at 2.2 kbase the message coding for β actin is seen. A close correlation between the levels of MDR1 message and the expressed protein is observed. However, the human MDR1 cDNA probe has very low levels of cross-reactivity with the mouse MDR1, and the quantity of human MDR1 message was quite variable in different extraction experiments. Thus, although the radioactivity of the hybridization probe could be quantitated, these experiments were not used for further quantitative estimation of MDR1 expression.

The immunoblot data reveal the total amounts of MDR1 in the given cell types, but may not reflect the plasma membrane insertion, required for the drug-extrusion function of this protein. In order to estimate the amount of MDR1 on the cell surface, flow-cytometry analysis was performed by using the UIC2 monoclonal antibody (Mechetner et al., supra), which reacts exclusively with extracellular epitope (s) of the human MDR1 protein.

The cell surface expression of MDR1 was measured by flow cytometry immunofluorescence (FIG. 4) in the same series of the KB human epidermoid cell lines examined above. Drug sensitive KB3, and increasingly drug resistant KB-V1, cells were labeled with a human MDR1-specific monoclonal antibody, UIC1, after which a FITC conjugated anti-mouse second antibody was applied. The intensity of cellular green fluorescence, indicative of the amount of bound UIC1, was determined by flow cytometry. Representative data are shown in FIG. 4 as cell numbers plotted against log value of FITC fluorescence. Filled histograms show the UIC2 labeled cells, while the isotype controls for each cell line are indicated as outlines.

Figure 5:
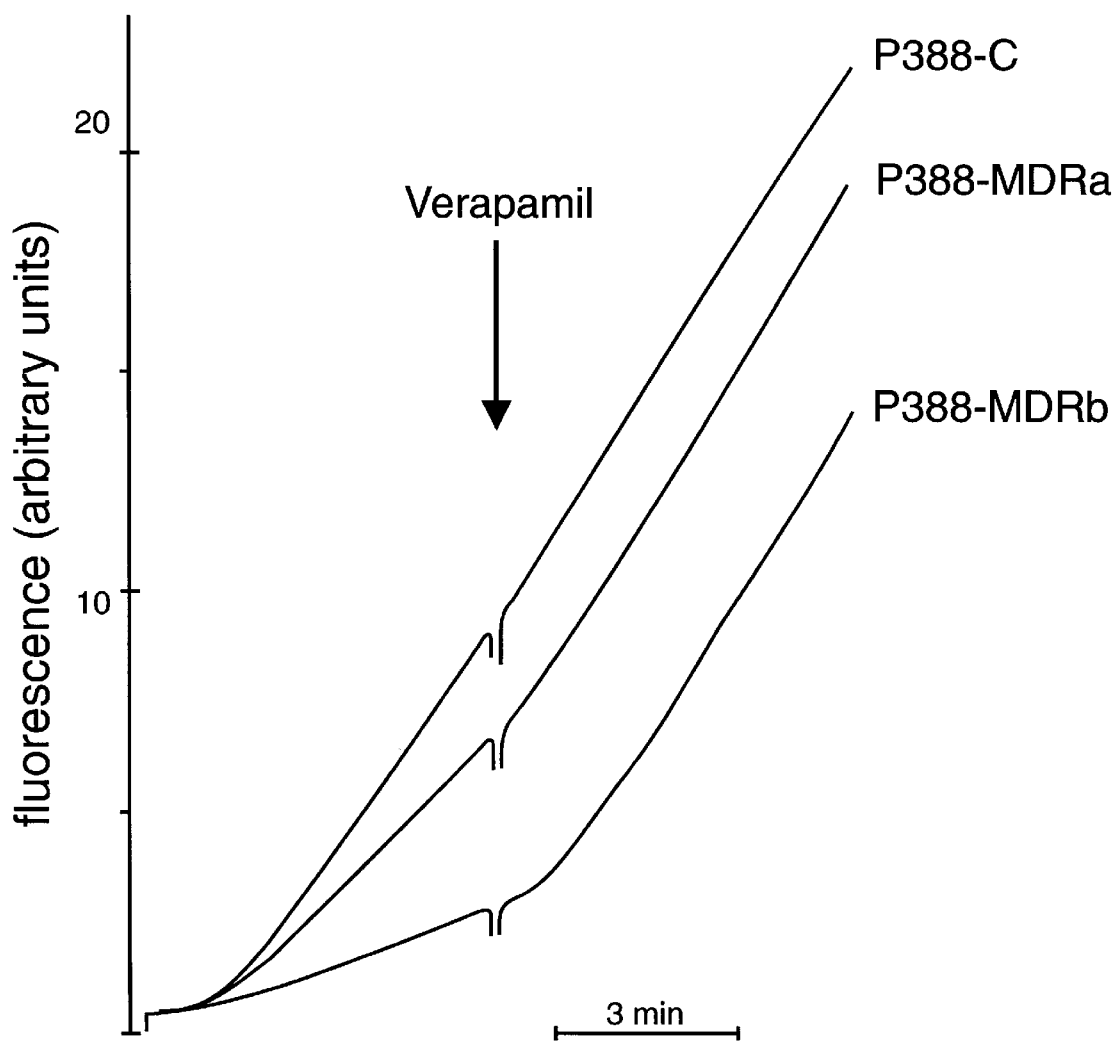
FIG. 5 is a graphical representation of the rate of calcein accumulation in drug-sensitive (P388-C) and drug resistant ($P^{388}$-$MDR_{a-c}$) cells measured by fluorometry.

The UIC2 antibody (visualized by a FITC labelled anti-mouse second antibody), reported the cell surface expression of the MDR1 protein in good accordance with the immunoblot data (FIG. 5). The cellular fluorescence obtained after UIC2 labeling was compared to labeling with isotype controls (indicated as an outline) of the same cell lines in each case.

In a series of similar experiments cell surface expression of human MDR1 was quantified by calculating the absolute fluorescence values for UIC2 binding in drug resistant KB, K562 and in human MDR1-transfected NIH 3T3 cells. In these experiments, with one exception (see below), a linear correlation was obtained between UIC2 binding and MDR1 levels measured by quantitative immunoblotting, with a correlation coefficient of r=0.970, p=1.57×10$^{-7}$.

EXAMPLE 6

Figure 8:
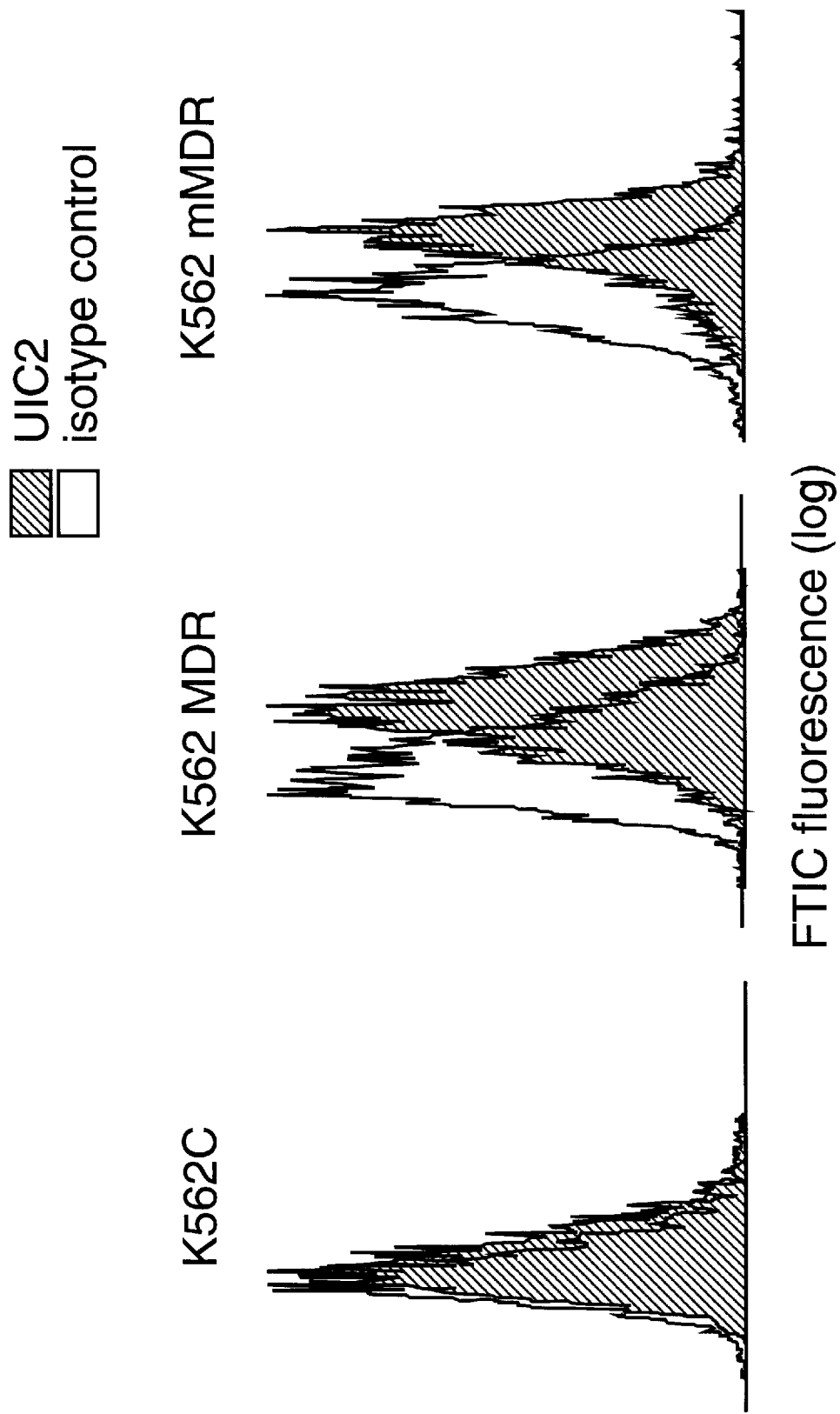
FIG. 8 is a plot showing the cell surface appearance of MDR1, measured by flow cytometry immunofluorescence, in K562 control cells, K562 drug resistant cells (MDR), and K562 cells that express a mutant MDR1 protein (mMDR).

Quantitative Assessment of MDR1 Protein Function in NIH 3T3 Fibroblasts, P388, Sf9, and KB Cells MDR1 protein function was quantified by measuring the extrusion of calcein-AM (Holló et al. supra), combined with a series of direct drug-cytotoxicity measurements (FIG. 8). Drug sensitive (P388-C) and drug-resistant (P$^{388}$-MDR$_{a-c}$) cells were incubated in the presence of 0.25 μM calcein-AM and fluorescence was measured in a spectrofluorimeter. After 5 minutes of incubation, an MDR reversing agent, verapamil (100 μM), was added to the medium. Data of a representative experiment are plotted as fluorescence (in arbitrary units) against time (FIG. 5).

As shown in FIG. 5, control P388 murine leukemia cells, in the presence of 0.25 μM calcein-AM, accumulated cellular calcein rapidly. The addition of 100 μM verapamil had practically no effect on either calcein fluorescence or its rate of accumulation. In contrast, in the MDR1-expressing P$^{388}_a$ cells, calcein accumulation is slow, and verapamil produces a rapid increase in the rate of dye uptake. This difference is even larger in the excessively drug-selected P$^{388}$b cells, in good correlation with the amount of the expressed MDR1 protein. When cell growth was measured in media containing different concentrations of adriamycin, the IC$_{50}$ values for the above presented three P388$_a$ cell lines were 0.5, 4, and 9 ng adriamycin/ml, respectively.

Similar experiments as shown in FIG. 5 were performed with all cell lines examined for MDR1 expression, and by using a relatively simple transport model the activity of the multi-drug transporter was expressed by a dimensionless parameter. Based on the assumptions and calculations described above, the following equation was used to determine the maximum activity of MDR1 in a given cell type:

$$\text{MDR1 activity factor } (f) = (F^* - F)/F^*, \qquad (1)$$

where F* is the rate of fluorescence increase before verapamil addition and F is the rate of fluorescence increase after the addition of excess verapamil, eliminating MDR1-dependent dye extrusion.

Figure 6:
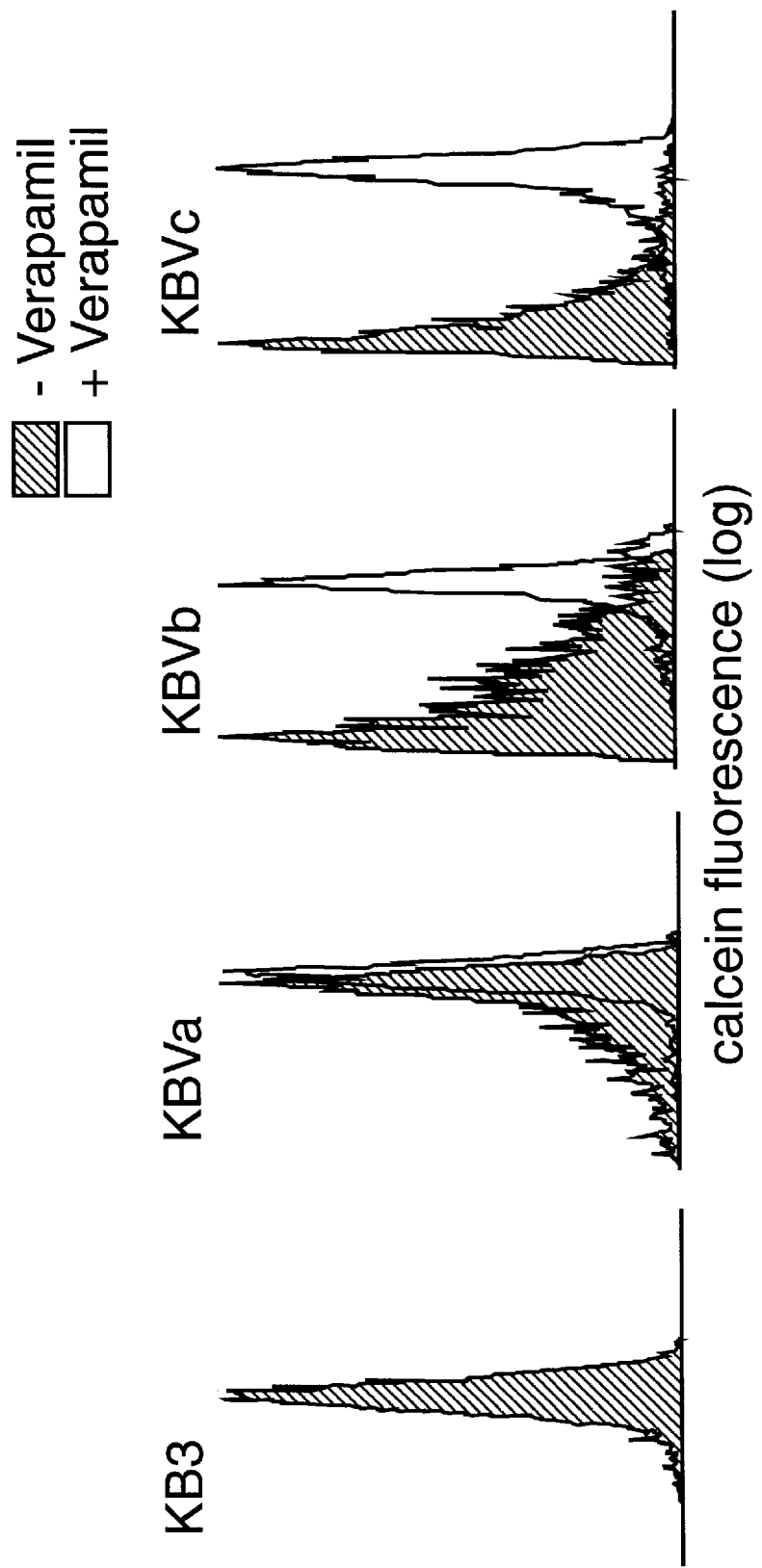
FIG. 6 is a plot of calcein accumulation in drug sensitive and increasingly drug-resistant KB cells measured by flow cytometry.

The correlation of the f value with the levels of MDR1 expression in the different cell types is shown in FIG. 6. As demonstrated, the solid line, drawn based on the equation of the model, fits the experimentally obtained values extremely well. In the case of low MDR1 expression levels the best fit is nearly a straight line, which provides an easy estimate of the maximum transport rate. In fact, according to our preliminary data obtained with leukocytes of hematological patients the clinically relevant levels of MDR1 are in this low expression range.

The above described f parameter, calculated from the calcein accumulation experiments, in most cases correlates with MDR1 expression and quantitatively describes the drug extrusion capacity (maximum activity) of the multi-drug transporter. In order to ensure this conclusion, the appropriate conditions for calcein-AM loading were examined in great detail. At pH values in the media between 7.0 to 7.8, at calcein-AM concentrations between 0.1–1 μM (verapamil=100 μM), and at cell numbers between 5×10$^4$/ml to 2×10$^6$/ml, the value of the f factor remained practically unchanged. Free calcein leakage was found to be extremely slow, its half-time being greater than 5 hours at 25° C. and 37° C., both in the control and the MDR1 expressing K562 cells. The effects of various inhibitors of MDR1 were also examined for their affect on calcein accumulation (Homolya et al., supra), and found that the nature of inhibition (competitive or non-competitive) does not influence the f value obtained. The important features of the inhibitor should be that it must not inhibit cellular esterase activity, or increase non-specific membrane permeability in the concentration range applied. This was found to be true for verapamil up to concentrations of 150 μM.

Figure 7:
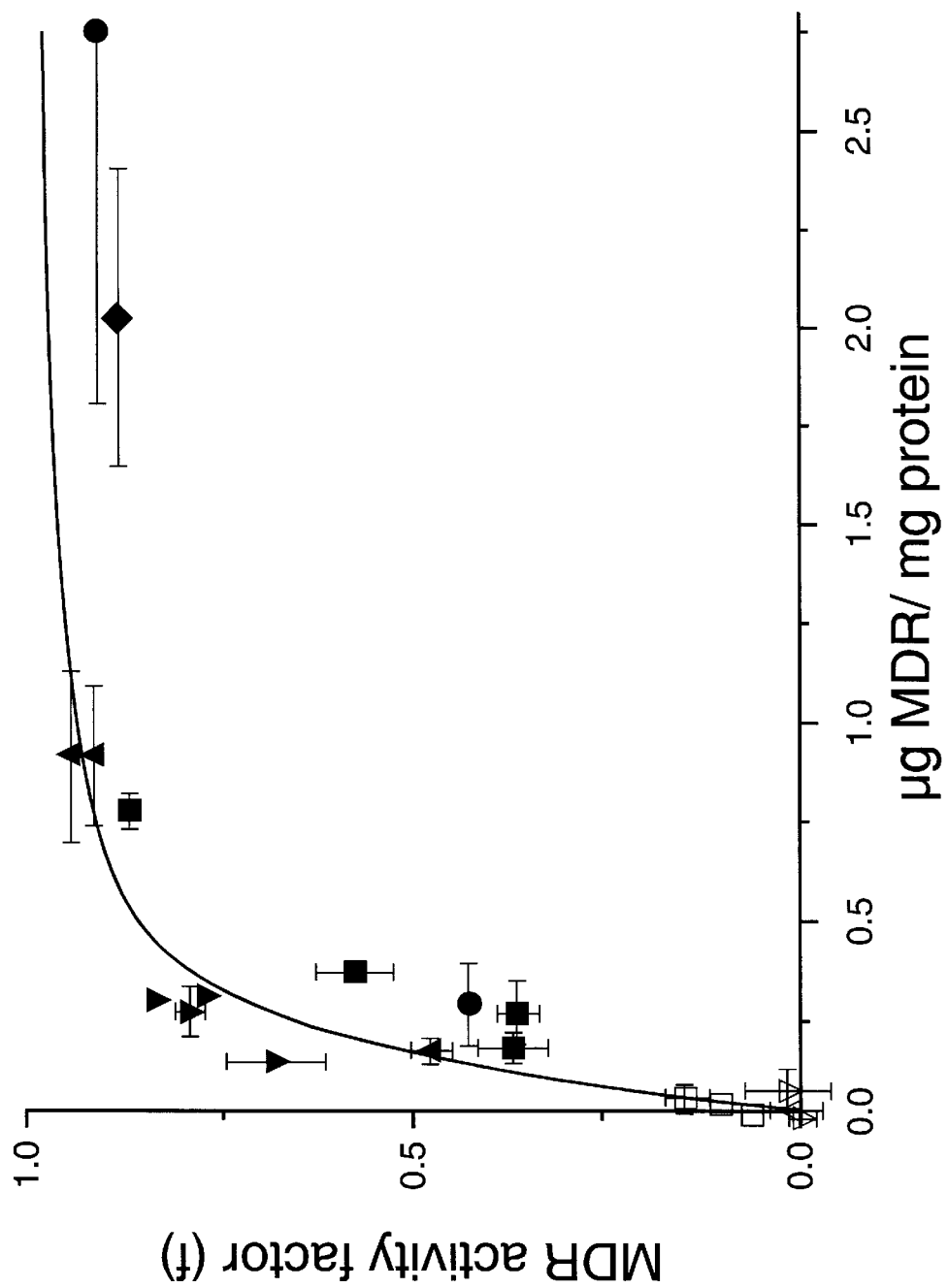
FIG. 7 is a graphical representation of the relationship between the amount of MDR1 expressed (measured by immunoblot) and the MDR1 activity factor (f).

FIG. 7 shows a comparison of between MDR1 expression and MDR1 function in different cell lines. MDR1 expression was quantitatively assessed by Western blotting. Cell lines with different level of MDR1 expression P388 MDR$_{a-b}$ (■), K562 MDR$_{a-b}$ (▼), KBV1$_{a-c}$ (▲), F4–6 (◆), 3T3 MDR1 (●); and their drug-sensitive counterparts P388 C (□), K562 C (▽), KB3 (Δ), 3T3 Control (○) were examined. MDR1 contents were determined by the 4077 polyclonal antibody and the HRP/ECL luminescence, as described above. The MDR activity factor (f) was calculated for each cell line by using the calcein accumulation rates determined before and after verapamil addition from the fluorometric time courses, shown in FIG. 5, and by using equation (1). The MDR activity factor (f)±the standard deviation (S.D.) is plotted against MDR1 contents±S.D. (in μg MDR1/mg cellular protein units). All data points represent at least three different determinations performed with the same cell batches. The curve was fitted to the points based on the mathematical model described by equation (9), and by using the non-linear least squares method. The value of parameter a was found to be $0.2680 \pm 7.76 \times 10^{-6}$, while the obtained value for parameter b was $0.0594 \pm 0.00002$ ($Chi^2 = 9.23 \times 10^{-10}$).

An important further advantage of the calcein accumulation method is its easy applicability for flow-cytometry studies. FIG. 6 demonstrates flow-cytometry measurement of calcein accumulation in the same series of drug-sensitive and drug-resistant KB cells as shown in FIG. 4. Drug sensitive KB3, and increasingly drug resistant KB-V1 cells (from the same cell lines as shown in FIG. 4) were loaded with 0.25 μM calcein in the absence or presence of 100 μM verapamil. The verapamil-pretreated cells are shown as an outline on the flow cytometry histogram (FIG. 6). $KBV1_{a-c}$ cells with gradually increasing MDR expression appear at lower fluorescence intensity, while preincubation of these cells with verapamil restores dye accumulation to the control level. The large difference obtained for cellular fluorescence by verapamil addition in the drug-resistant cells clearly reflects the calcein-AM extrusion by MDR1. For the calculation of the MDR1 activity (f) factor from the flow cytometry data, the absolute fluorescence values were calculated from mean channel values and inserted into the above described simple equation (1). The f values obtained from cell population and flow cytometry fluorescence measurements gave a excellent linear correlation.

EXAMPLE 7

Applicability of the Morphological and Functional Assays to Determine Multi-Drug-Resistance As described above, the levels of MDR1 protein expression and its cell surface appearance closely correlated with the multi-drug transporter activity in the different cell types. However, this correlation does not exist when the MDR1 is in a non-functional form. Applicants have studied a non-functional form of MDR1 which is expressed by human erythroleukemia (K562) cells.

When analyzing various drug-selected and unselected strains of the K562 cell line, one batch of the previously drug resistant cells, kept for several passages in drug-free media, developed into a clone expressing large amounts of the MDR1 protein. The MDR1 protein, detected as a broad band on the immunoblot of the protein extract from these cells (labeled as K562/mMDR), was mostly glycosylated and greatly exceeded the level of MDR1 expression in the drug-resistant K562 cells (K562/MDR), almost reaching the amount expressed in the MDR1-transfected NIH 3T3 fibroblasts. Membrane proteins of the K562 Control (C), drug resistant (MDR) and a mutant MDR1 expressing (mMDR) cells were immunoblotted with the 4077 polyclonal antibody. Membrane proteins of the Sf9 insect cell line (Sf9+ MDR), infected by a human MDR1-baculovirus construct were used as standard for these experiments. An immunublot of the membrane preparation from retrovirally transformed MDR1 expressing NIH 3T3 G185 cells is shown for comparison. Each lane contained 20 μg protein obtained from TCA-precipitated preparations of cells, except for the lane of MDR1-expressing Sf9 insect cells, which contained 2 μg protein from isolated membranes. The numbers below the lanes represent the quantitatively determined MDR1 protein amounts in μg MDR1/mg cellular protein units.

In FIG. 8, flow cytometry measurements demonstrated the cell surface expression of MDR1 in drug sensitive, drug resistant, and mutant MDR1 (K562 mMDR) expressing K562 cells. Immunofluorescence labeling was carried out with the UIC2 monoclonal antibody and by a FITC conjugated second antibody. Data are expressed as cell number versus log FITC fluorescence. The corresponding isotype controls are indicated as an outline on the histograms. Surface expression of MDR1 in the K562/mMDR cells, detected by UIC2, was also quite pronounced, although not significantly exceeding the levels seen in the K562/MDR cells. This is the case when the correlation between the determinations of MDR1 by Western blotting and by surface labeling was different from that found in other cell types (as mentioned above), which is probably due to the fact that a part of the overexpressed mutant protein is not fully glycosylated and may be partially trapped in the endoplasmic reticulum.

Figure 9:
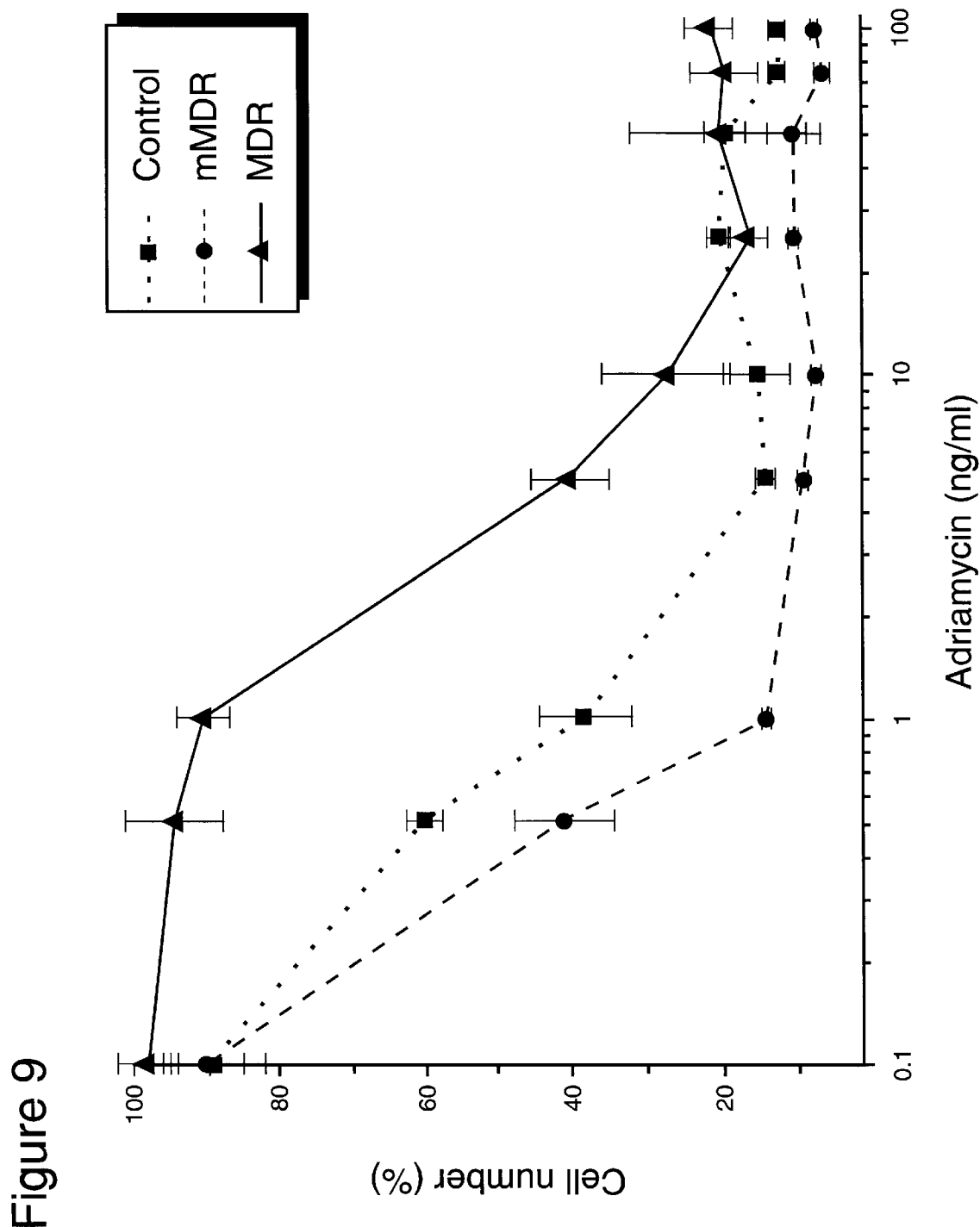
FIG. 9 is a graphical representation of the number of surviving cells (cell number %) versus adriamycin concentration (ng/ml) for K562 control cells, K562 drug resistant cells (MDR), and K562 cells expressing a mutant MDR1 protein (mMDR).

Cell survival was measured in control, MDR1-expressing, and mutant MDR1-expressing(mMDR1) K562 cells. K562/mMDR cells, in contrast to K562/MDR cells, did not show an increased resistance against adriamycin and were non-resistant to vincristine (FIG. 9). To assess drug resistance of the control (■), MDR1 (♦) and mutant MDR1 (●) expressing K562 cells, cell survival was studied by culturing in the presence of the cytotoxic agent adriamycin (FIG. 9). Cells were grown in the presence of adriamycin (0.1–100 ng/ml) for three days and absolute cell numbers were determined on the third day. Data are expressed as mean cell number (% of original)±S.E.M. against adriamycin concentrations, calculated from three independent parallel experiments.

Correlating with this absence of drug-resistance, the K562/mMDR cells did not show any verapamil-sensitive calcein-AM extrusion either in fluorometry or flow cytometry measurements (FIG. 10). Calcein accumulation was assayed as described for FIG. 9. Cells pretreated with verapamil (100 μM) for 5 minutes are plotted as an outline in the corresponding histograms. Representative data are expressed as cell numbers versus log calcein fluorescence in arbitrary units. Drug resistant K562 cells accumulated much smaller amounts of calcein than the control or the mutant (m)MDR1-expressing cells. Similarly to the control cells, calcein accumulation was high in the K562/mMDR cells and verapamil had no effect on this dye accumulation. In contrast, the K562/MDR cells, although with a lower level of MDR1 expression (see FIG. 8), showed an increased resistance against adriamycin (FIG. 9) and a significant calcein-AM extrusion (FIG. 10) that can be inhibited by verapamil.

EXAMPLE 8

Use of the Calcein Assay for Clinical Diagnosis

The invention provides a rapid and quantitative assay for diagnosing multi-drug resistance in cells from a patient. Although the level of MDR1 protein expression provides one measure of multi-drug resistance, expression of a non-functional, or mutant, form of MDR1 can lead to misleading results. A functional test, such as the one provided herein, furnishes a more direct measure of multi-drug resistant activity, and thus a more relevant clinical diagnosis.

The assay of the invention can be conducted on a variety of cell types. The test can be conducted using any type of cell that can be grown in suspension, e.g., white blood cells. The test can also be conducted using cells that can be grown on cover slips, e.g., fibroblasts, or any surface-attaching normal and/or tumor cells. In fact, any sample of cells that can be transformed into a suspension, or examined under a microscope or in a fluorometer, e.g., native slices of tissues. Cells are collected from the body of an animal, e.g., a human patient, by withdrawal of bodily fluid, e.g., blood plasma, by biopsy of tissue, e.g., cancerous tissue, or by a cellular swab.

The assay of the invention is accompanied by positive and negative control experiments in order to evaluate the results. For example, negative control cells are known to those of skill in the art, and are provided herein, e.g., NIH 3T3 fibroblasts, P388 cells, Sf9 cells, and KB3 cells. Positive control cells are made available by stably integrating a gene expressing the MDR1 protein into any of the same cell types used for the negative cells, as demonstrated above, or by repeated incubations of the negative cells in media containing appropriate cytotoxic agents, e.g., vincristine or adriamycin.

Alternatively, the assay can be conducted using an internal "self" control composed of a portion of the same sample of cells withdrawn from the patient. One portion of the cell sample is assayed for calcein accumulation as described above. If the sample is multi-drug resistant the level of calcein accumulation is expected to be low. As a control, the other portion of the cell sample is treated with an inhibitor of multi-drug resistance, e.g., verapamil. If the original biological sample is multi-drug resistant, calcein accumulation will rise with the addition of verapamil; in contrast, if the sample is not multi-drug resistant (low calcein accumulation being due to a false positive result) the inhibitor will not overcome the multi-drug resistant effect, and calcein accumulation will remain low. An internal control can also be performed by adding an inhibitor of multi-drug resistance to the biological test samples during the incubation period, as demonstrated in Example 2 (FIG. 1).

Other embodiments are within the claims set forth below. What is claimed is:

1. A method of detecting multi-drug resistance in a biological specimen, said method comprising the steps of:
   (a) exposing cells of a biological specimen to a calcein compound that is an acetoxymethyl ester or acetate ester of calcein; and
   (b) measuring free calcein accumulating in said specimen cells relative to control cells, reduced free calcein accumulation in specimen cells relative to control cells indicating the presence of multi-drug resistance in said biological specimen.

2. The method of claim 1, wherein said measuring comprises fluorometry.

3. The method of claim 1, wherein said measuring comprises flow cytometry.

4. The method of claim 1, wherein said measuring comprises cell imaging.

5. The method of claim 1, further comprising the step of measuring the survival of cells in said specimen.

6. The method of claim 1, further comprising the step of determining the amount of a multi-drug transporter protein made by said specimen cells.

7. The method of claim 1, further comprising the step of determining the amount of a multi-drug transporter protein on the surface of said specimen cells.

8. The method of claim 1, wherein said biological sample is from a mammal.

9. The method of claim 8, wherein said mammal is a human.

10. The method of claim 1, wherein said method is used to diagnose resistance to a therapeutic compound.

11. The method of claim 10, wherein said therapeutic compound is a chemotherapeutic compound.

12. The method of claim 10, wherein said therapeutic compound is an antibiotic compound.

13. The method of claim 1, wherein said control cells are a portion of said biological sample, and said method further comprises exposing said control cells to an inhibitor of multi-drug resistance.

14. The method of claim 1, wherein said measuring comprises calculating an activity factor (f) which is representative of the level of multi-drug resistance in said sample.

15. The method of claim 13, wherein said measuring comprises calculating an activity factor (f) which is representative of the level of multi-drug resistance in said sample.

16. A kit comprising instructions for detecting multi-drug resistance in a biological specimen, wherein said instructions teach the method of any one of claims 1 or 13.

17. The kit of claim 16, wherein said kit further comprises a calcein compound.

18. The kit of claim 16, wherein said kit further comprises an inhibitor of multi-drug resistance.

* * * * *